(12) United States Patent
Mikami et al.

(10) Patent No.: US 8,507,711 B2
(45) Date of Patent: Aug. 13, 2013

(54) FLAME-RETARDANT COMPOUND, FLAME-RETARDANT PARTICLE, RESIN COMPOSITION AND RESIN FORMED BODY

(75) Inventors: Masato Mikami, Kanagawa (JP); Masayuki Okoshi, Kanagawa (JP); Kazuya Yamanoi, Kanagawa (JP)

(73) Assignee: Fuji Xerox Co., Ltd., Tokyo (JP)

( * ) Notice: Subject to any disclaimer, the term of this patent is extended or adjusted under 35 U.S.C. 154(b) by 0 days.

(21) Appl. No.: 13/331,825

(22) Filed: Dec. 20, 2011

(65) Prior Publication Data

US 2012/0088871 A1   Apr. 12, 2012

Related U.S. Application Data

(62) Division of application No. 12/174,253, filed on Jul. 16, 2008, now abandoned.

(30) Foreign Application Priority Data

Oct. 2, 2007   (JP) .................................. 2007-259087

(51) Int. Cl.
| | | |
|---|---|---|
| C07C 69/017 | (2006.01) | |
| C07C 69/94 | (2006.01) | |
| B32B 5/16 | (2006.01) | |

(52) U.S. Cl.
USPC ........... 558/270; 558/272; 558/274; 558/275; 558/288; 428/402; 428/403

(58) Field of Classification Search
CPC .............................. C07C 69/017; C07C 69/94
USPC ........................ 558/270–275, 288
See application file for complete search history.

(56) References Cited

U.S. PATENT DOCUMENTS

| | | | |
|---|---|---|---|
| 3,765,837 A | 10/1973 | Aycock et al. | |
| 3,978,024 A | 8/1976 | Mark | |
| 4,032,510 A | 6/1977 | Floyd et al. | |
| 4,096,169 A * | 6/1978 | Chalk ........................... | 558/268 |
| 4,104,217 A | 8/1978 | Leistner et al. | |
| 4,209,431 A | 6/1980 | Clark et al. | |
| 4,380,612 A | 4/1983 | Mark et al. | |
| 4,535,108 A | 8/1985 | Rosenquist et al. | |
| 4,714,746 A * | 12/1987 | Serini et al. .................... | 525/439 |
| 4,873,279 A * | 10/1989 | Nelson ........................... | 524/384 |
| 6,160,156 A * | 12/2000 | Reisinger et al. ............. | 558/274 |
| 7,223,811 B2 | 5/2007 | Nagy et al. | |
| 7,348,458 B2 | 3/2008 | Nishimi et al. | |
| 7,511,092 B2 * | 3/2009 | Glasgow et al. .............. | 524/298 |
| 2006/0089444 A1 | 4/2006 | Goodman et al. | |
| 2007/0082989 A1 * | 4/2007 | Glasgow et al. .............. | 524/284 |
| 2009/0087659 A1 * | 4/2009 | Mikami et al. ................. | 428/403 |

FOREIGN PATENT DOCUMENTS

| | | |
|---|---|---|
| JP | 53-074557 | 7/1978 |
| JP | A-54-091557 | 7/1979 |
| JP | A-62-015256 | 1/1987 |
| JP | A-06-025469 | 2/1994 |
| JP | A-06-200141 | 7/1994 |
| JP | A-10-279694 | 10/1998 |
| JP | A-2001-181342 | 7/2001 |
| JP | A-2003-003059 | 1/2003 |
| JP | A-2003-292816 | 10/2003 |
| JP | A-2004-292412 | 10/2004 |
| JP | A-2004-331709 | 11/2004 |
| JP | A-2005-520873 | 7/2005 |
| JP | A-2005-521767 | 7/2005 |

OTHER PUBLICATIONS

Tokyo Chemical Industry, LTD.; Safety Data Sheet: Diphenyl Carbonate; Sep. 25, 2007.
Tokyo Chemical Industry, LTD.; Safely Data Sheet: Guaiacol Carbonate; Jul. 9, 2006.

* cited by examiner

*Primary Examiner* — Hoa (Holly) Le
(74) *Attorney, Agent, or Firm* — Oliff and Berridge, PLC

(57) ABSTRACT

A flame-retardant compound has a structure represented by formula (2):

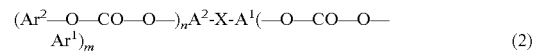

wherein $A^1$ and $A^2$ each independently represents a substituted or unsubstituted aromatic group;
X represents a divalent group represented by —S—, —O—, —CO—, —CN—, —CH$_2$—, —C(CH$_3$)$_2$—, —CH(CH$_3$)—, —NH—, —SO— or —SO$_2$—;
$Ar^1$ and $Ar^2$ each independently represents a substituted or unsubstituted phenyl group; and
m and n each independently represents an integer of 1 to 3.

22 Claims, 1 Drawing Sheet

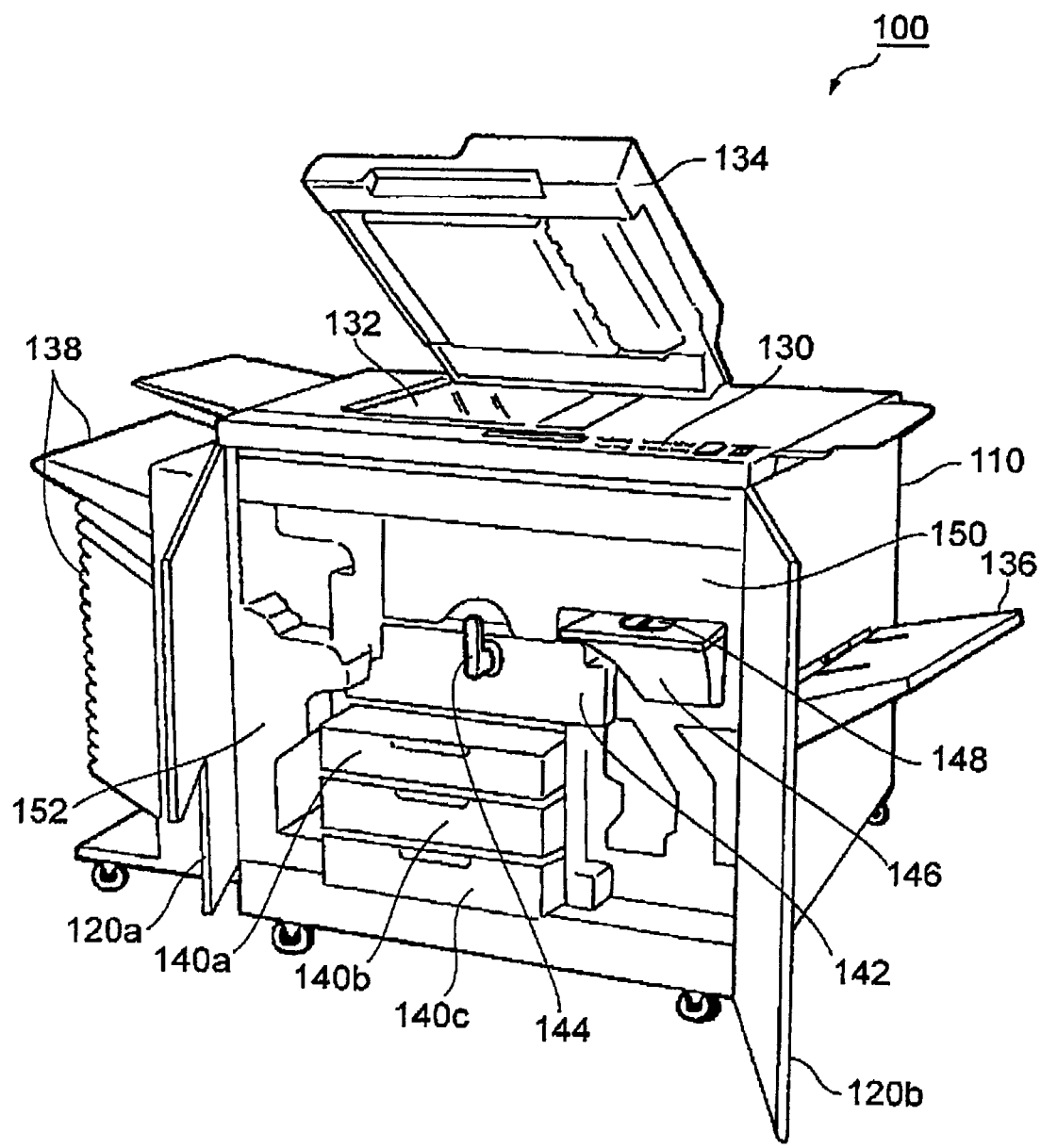

FLAME-RETARDANT COMPOUND, FLAME-RETARDANT PARTICLE, RESIN COMPOSITION AND RESIN FORMED BODY

CROSS-REFERENCE TO RELATED APPLICATION

This is a Divisional of application Ser. No. 12/174,253 filed Jul. 16, 2008, which claims priority of Japanese Patent Application No. 2007-259087 filed Oct. 2, 2007. The disclosure of these applications is hereby incorporated by reference herein in their entirety.

BACKGROUND

Technical Field

The present invention relates to a flame-retardant compound, a flame-retardant particle, a resin composition and a resin formed body.

SUMMARY

According to an aspect of the invention, there is provided a flame-retardant compound that has a structure represented by formula (1):

$$—X-A^1(—O—CO—O—Ar^1)_m \quad (1)$$

wherein $A^1$ represents a substituted or unsubstituted aromatic group;

X represents a divalent group represented by —S—, —O—, —CO—, —CN—, —CH$_2$—, —C(CH$_3$)$_2$—, —CH(CH$_3$)—, —NH—, —SO— or —SO$_2$—;

$Ar^1$ represents a substituted or unsubstituted phenyl group; and m represents an integer of 1 to 3.

BRIEF DESCRIPTION OF THE DRAWING

Exemplary embodiments of the present invention will be described in detail based on the following figures, wherein:

FIG. 1 illustrates an outer appearance perspective view showing an image forming apparatus comprising a casing according to one exemplary embodiment of the resin formed body of the present invention.

DETAILED DESCRIPTION

Preferred exemplary embodiments are described in detail below possibly by referring to the drawings.

(Flame-Retardant Compound)

The flame-retardant compound according to the first exemplary embodiment has a structure represented by the following formula (1):

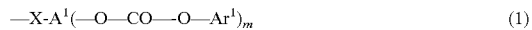
$$—X-A^1(—O—CO—O—Ar^1)_m \quad (1)$$

[wherein $A^1$ represents a substituted or unsubstituted aromatic group, X represents a divalent group represented by —S—, —O—, —CO—, —CN—, —CH$_2$—, —C(CH$_3$)$_2$—, —CH(CH$_3$)—, —NH—, —SO— or —SO$_2$—, $Ar^1$ represents a substituted or unsubstituted phenyl group, and m represents an integer of 1 to 3].

The flame-retardant compound according to this exemplary embodiment is used for the same usage as that of the conventional flame retarder. For example, the compound is used by dispersing it in a resin to impart flame retardance. When the flame-retardant compound according to this exemplary embodiment is dispersed in a resin, the structure represented by formula (1) forms a carbonized layer (char) at the burning, so that the cycle of burning reaction can be prevented and flame retardance can be brought out.

In formula (1), $A^1$ represents a substituted or unsubstituted aromatic group. The substituent is not particularly limited, but examples thereof include an alkyl group having a carbon number of 1 to 10, a phenyl group, an alkoxyl group, an amino group, an amido group, an aryl group, an acyl group, a vinyl group, an allyl group, a hydroxy group, an ester group and a carboxyl group. Also, the substituent is not particularly limited in its number and position.

In formula (1), X represents a divalent group represented by —S—, —O—, —CO—, —CN—, —CH$_2$—, —C(CH$_3$)$_2$—, —CH(CH$_3$)—, —NH—, —SO— or —SO$_2$— but is preferably —S—, —CN—, —SO— or —SO$_2$—, because the compound forms a carbonized layer at the burning and contributes to enhancement of the flame retardance. Incidentally, in the flame-retardant compound according to the first exemplary embodiment, the above-described substituent of $A^1$ may constitute X. Furthermore, when two or more characteristic groups represented by —O—CO—O—$Ar^1$ in formula (1) are present, —O— in one characteristic group may constitute X. That is, a compound where two or more characteristic groups represented by —O—CO—O—$Ar^1$ bonded to $A^1$ are present satisfies the structure represented by formula (1). In formula (1), $Ar^1$ represents a substituted or unsubstituted phenyl group. The substituent is not particularly limited, but examples thereof include an alkyl group having a carbon number of 1 to 10, a phenyl group, an alkoxyl group, an amino group, an amido group, an aryl group, an acyl group, a vinyl group, an allyl group, a hydroxy group, an ester group and a carboxyl group. Also, the substituent is not particularly limited in its number and position. In formula (1), m represents an integer of 1 to 3.

In producing the flame-retardant compound having a structure represented by formula (1), for example, an aromatic compound described below is used. Examples of the aromatic compound include cresol, aminophenol, hydroxybenzonitrile, hydroxybenzaldehyde, dimethylphenol, nitrosophenol, 5-amino-2-methoxyphenol, 2-methoxy-5-nitrophenol, 2-methoxy-4-nitrophenol, 2-amino-3-methylphenol, difluorophenol, hydroquinone, hydroxybenzenephenone, hydroxybenzyl alcohol, phenylhydroquinone, 4-nitro-1,2-benzenediol, 3,5-dinitro-1,2-benzenediol, 3-methyl-1,2-benzenediol, phloroglucinol, phloroglucinolcarboxylic acid and 4,6-dinitro-1,2,3-benzenetriol, and examples of the aromatic compound containing a sulfuric acid group include hydroxybenzenesulfonic acid, 3-amino-4-hydroxybenzenesulfonic acid, 3-amino-4-hydroxy-5-nitrobenzenesulfonic acid, 4-hydroxy-3-nitroso-1-naphthalenesulfonic acid, 4,5-hydroxy-1,3-benzenedisulfonic acid, 4,5-hydroxy-5-nitro-1,3-benzenedisulfonic acid and salts thereof. Among these, in view of flame retardance, a compound having a sulfuric acid group is preferred.

Such an aromatic compound and a compound having a characteristic group represented by —CO—O—$Ar^1$ in formula (1) are reacted, whereby the flame-retardant compound having a structure represented by formula (1) is obtained.

Examples of the compound having the above-described characteristic group include phenyl chloroformate and phenyl bromoformate.

The reaction of the aromatic compound and the compound having the above-described characteristic group is performed in the presence of an amine which is a reaction accelerator. The amine is not particularly limited, but examples thereof include triethylamine, diethylaniline, pyridine, dimethylaniline, quinoline, and N,N,N',N'-tetramethylethylenediamine.

Other than the reaction above, a melt trans-esterification of a diaryl carbonate in the presence of a basic catalyst may also be performed. The diaryl carbonate is not particularly limited, but examples thereof include diphenyl carbonate. Also, the basic catalyst is not particularly limited, but examples thereof include an alkali metal, an alkaline earth metal, a basic metal compound such as zinc oxide, a metal carbonate, a metal acetate, a metal hydride, a quaternary ammonium salt, a phosphonium salt, and 4-dimethylaminopyridine.

The flame-retardant compound according to the second exemplary embodiment has a structure represented by the following formula (2):

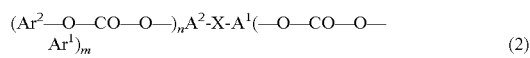
(2)

[wherein $A^1$ and $A^2$ each independently represents a substituted or unsubstituted aromatic group, X represents a divalent group represented by —S—, —O—, —CO—, —CN—, —CH$_2$—, —C(CH$_3$)$_2$— —CH(CH$_3$)—, —NH—, —SO— or —SO$_2$—, $Ar^1$ and $Ar^2$ each independently represents a substituted or unsubstituted phenyl group, and m and n each independently represents an integer of 1 to 3].

The flame-retardant compound according to this exemplary embodiment is used for the same usage as that of the conventional flame retarder. For example, the compound is used by dispersing it in a resin to impart flame retardance. When the flame-retardant compound according to this exemplary embodiment is dispersed in a resin, the structure represented by formula (2) forms a carbonized layer (char) at the burning, so that the cycle of burning reaction can be prevented and flame retardance can be brought out.

In formula (2), $A^1$ and $A^2$ each independently represents a substituted or unsubstituted aromatic group. The substituent is not particularly limited, but examples thereof include an alkyl group having a carbon number of 1 to 10, a phenyl group, an alkoxyl group, an amino group, an amido group, an aryl group, an acyl group, a vinyl group, an allyl group, a hydroxy group, an ester group and a carboxyl group. Also, the substituent is not particularly limited in its number and position.

In formula (2), X represents a divalent group represented by —S—, —O—, —CO—, —CN—, —CH$_2$—, C(CH$_3$)$_2$—, —CH(CH$_3$)—, —NH—, —SO— or —SO$_2$— but is preferably —S—, —CN—, —SO— or —SO$_2$—, because a carbonized layer is formed at the burning and contributes to enhancement of the flame retardance.

In formula (2), $Ar^1$ and $Ar^2$ each independently represents a substituted or unsubstituted phenyl group. The substituent is not particularly limited, but examples thereof include an alkyl group having a carbon number of 1 to 10, a phenyl group, an alkoxyl group, an amino group, an amido group, an aryl group, an acyl group, a vinyl group, an allyl group, a hydroxy group, an ester group and a carboxyl group. Also, the substituent is not particularly limited in its number and position. In formula (2), m and n each independently represents an integer of 1 to 3.

In producing the flame-retardant compound having a structure represented by formula (2), for example, an aromatic compound described below is used. Examples of the aromatic compound include 4,4'-thiodiphenol, resorcinol sulfide, 4,4'-sulfonyldiphenol, resorcinol sulfoxide, 4,4'-sulfonylbis(2-methylphenol), 4,4'-sulfonylbis(2,6-dimethylphenol), bisphenol A, 4,4'-dihydroxydiphenyl ether, 4,4'-ethylidenebisphenol, 4,4'-propylidenebisphenol, 2,2-bis-(4-hydroxyphenyl)-butane, 2,2-bis(4-hydroxy-3-methylphenyl)propane, and 1,1,1-tris(4-hydroxyphenyl)ethane.

Such an aromatic compound and a compound having a characteristic group represented by —CO—O—$Ar^1$ or —CO—O—$Ar^2$ in formula (2) are reacted, whereby the flame-retardant compound having a structure represented by formula (2) is obtained.

As for the compound having the above-described characteristic group, those described above in the first exemplary embodiment are used. The reaction of the aromatic compound and the compound having the above-described characteristic group is performed in the presence of an amine which is a reaction accelerator. As for the amine, those described above in the first exemplary embodiment are used.

Other than the reaction above, a melt trans-esterification of a diaryl carbonate in the presence of a basic catalyst may also be performed. The diaryl carbonate is not particularly limited, but examples thereof include diphenyl carbonate. Also, the basic catalyst is not particularly limited, but examples thereof include an alkali metal, an alkaline earth metal, a basic metal compound such as zinc oxide, a metal carbonate, a metal acetate, a metal hydride, a quaternary ammonium salt, a phosphonium salt, and 4-dimethylaminopyridine.

The flame-retardant compound according to the first and second exemplary embodiments may be dispersed in a resin as it is or may be dispersed in a resin after forming it into a particle state.

(Flame-Retardant Particle)

The flame-retardant particle according to the third exemplary embodiment comprises a particle (hereinafter referred to as a "core particle") having formed on the surface thereof a surface coat layer containing the flame-retardant compound according to the first or second exemplary embodiment.

The flame-retardant particle according to this exemplary embodiment is used for the same usage as that of the conventional flame retarder. For example, the particle is used by dispersing it in a resin to impart flame retardance. When the flame-retardant particle according to this exemplary embodiment is dispersed in a resin, the flame-retardant compound forms a carbonized layer (char) at the burning, so that the cycle of burning reaction can be prevented and flame retardance can be brought out.

Here, examples of the core particle include a particle comprising an inorganic material, an inorganic material complex, an organic polymer, a dendrimer, clay, fullerene or carbon nanotube.

The surface coat layer is not particularly limited as long as it is a layer containing at least above-described flame-retardant compound. For example, the surface coat layer may contain, in addition to the flame-retardant compound, as a synthetic material, a polymer material such as polystyrene, polyacrylic acid derivative, polyacrylic acid derivative, polyethylene, polypropylene, phenol resin, furan resin, xylene-formaldehyde resin, urea resin, melamine resin, aniline resin, alkyd resin, unsaturated polyester, epoxy resin, poly-p-xylylene, polyvinyl acetate, acrylic resin, methacrylic resin, polyvinyl chloride, polyvinylidene chloride, fluorine-based plastic, polyacrylonitrile, polyvinyl ether, polyvinyl ketone, polyether, polycarbonate, thermoplastic polyester, polyamide, diene-based plastic, polyurethane-based plastic, polyphenylene, polyphenylene oxide, polysulfone, aromatic heterocyclic polymer, silicone, natural rubber-based plastic, or a mixed material (polymer blend) of two or more species of these polymer materials; or a material comprising a naturally-occurring organic polymer, such as xanthan gum, agarose, agaropectin, amylose, sodium alginate, propylene glycol alginate, isolichenan, insulin, ethyl cellulose, ethyl hydroxyethyl cellulose, curdlan, casein, carrageenan, carboxymethyl cellulose, carboxymethyl starch, callose, agar, chitin, chitosan, silk fibroin, guar gum, quince seed, Crown Gall polysaccharide, glycogen, glucomannan, keratan sulfate, keratin protein, collagen, cellulose acetate, gellan gum, schizophyllan, gelatin, ivory nut mannan, tunicin, dextran, dermatan sulfate, starch, tragacanth gum, nigeran, hyaluronic acid, hydroxyethyl cellulose, hydroxypropyl cellulose, pustulan, funoran, degraded xyloglucan, pectin, porphyran, methyl cellulose, methyl starch, laminaran, lichenan, lentinan or locust bean gum.

The method for forming the surface coat layer is not particularly limited, but examples thereof include a wet coating method of dissolving the flame-retardant compound in a solvent and coating the solution, and a dry method such as melt coating and mechanical coating.

The coverage of the surface coat layer is preferably mass % or more of the entirety of the surface-coated flame-retardant particle. If the coverage is less than 5 mass %, the flame retardance cannot be effectively obtained.

In the case of using a porous particle as the core particle in the flame-retardant particle according to this exemplary embodiment, the constituent material of the surface coat layer may fill in pores of the porous particle. Also, in the flame-retardant particle according to this exemplary embodiment, a layer other than the surface coat layer may be further provided on the core particle within the range not impairing the effects of the present invention.

The flame-retardant particle according to the fourth exemplary embodiment comprises a particle (core particle) having introduced into the surface thereof a structure represented by formula (1)

The flame-retardant particle according to this exemplary embodiment is used for the same usage as that of the conventional flame retarder. For example, the particle is used by dispersing it in a resin to impart flame retardance. When the flame-retardant particle according to this exemplary embodiment is dispersed in a resin, the structure represented by formula (1) bonded to the surface of the core particle forms a carbonized layer (char) at the burning, so that the cycle of burning reaction can be prevented and flame retardance can be brought out. Also, the resin formed body is prevented from drip at the burning.

Here, examples of the core particle include a particle comprising an inorganic material, an inorganic material complex, an organic polymer, a dendrimer, clay, fullerene or carbon nanotube.

The core particle is not particularly limited as long as it has a functional group on the surface and allows for introduction of a compound represented by formula (1). Examples of the functional group on the core particle surface include a hydroxyl group, a carboxyl group, an amino group, an aldehyde group, a vinyl group, a carbonyl group, a nitro group, a sulfo group, an ether group, an ester group, an amide group, an isocyanate group, a halogen group, an alkyl group and a cyano group, and although the functional group is not particularly limited as long as it can be chemically bonded, a hydroxyl group is preferred in view of easy reaction or simple process.

The method for introducing a structure represented by formula (1) into the core particle is not particularly limited, and the structure is introduced by reacting a compound having a structure represented by formula (1) with a functional group on the core particle surface by a known method.

Also, after previously introducing a structure represented by $—X—$ or $—X-A^{1'}$ of formula (1), a structure represented by $-A^1(—O—CO—O—Ar^1)_m$ or $(—O—CO—O—Ar^1)_m$ may be introduced. In this case, a method of treating the core particle with a silane coupling agent to introduce a structure represented by $—X—$ or $—X-A^{1'}$ and then introducing a structure represented by $-A^1(—O—CO—O—Ar^1)_m$ or $(—O—CO—O—Ar^1)_m$ is used. In the formula above, $A^{1'}$ is a group which becomes $A^1$ when bonded to the structure represented by $(—O—CO—O—Ar^1)_m$.

Examples of the silane coupling agent include those containing a vinyl functional group having radical polymerizability, such as vinyltrichlorosilane, vinyltrimethoxysilane and vinyltriethoxysilane; those containing an acryloxy functional group, such as 3-acryloxypropyltrimethoxysilane; those containing a methacryloxy functional group, such as 3-methacryloxypropylmethyldimethoxysilane, 3-methacryloxypropyltrimethoxysilane, 3-methacryloxypropylmethyldiethoxysilane and 3-methacryloxypropyltriethoxysilane; those containing an epoxy functional group having polycondensability, such as 2-(3,4-epoxycyclohexyl)ethyltrimethoxysilane, 3-glycidoxypropyltrimethoxysilane, 3-glycidoxypropylmethyldiethoxysilane and 3-glycidoxypropyltriethoxysilane; those containing an amino functional group, such as N-2-(aminoethyl)-3-aminopropylmethyldimethoxysilane, N-2-(aminoethyl)-3-aminorpopyltrimethoxysilane, N-2-(aminoethyl)-3-aminopropyltriethoxysilane, 3-aminopropyltrimethoxysilane and 3-aminorpopyltriethoxysilane; and those containing a chloropropyl functional group, such as 3-chloropropyltrimethoxysilane.

It may be also possible to treat the core particle with a silane coupling agent, introduce an aromatic group by a reaction with an aromatic compound and then introduce a structure represented by $(—O—CO—O—Ar^1)_m$.

In this exemplary embodiment, the functional group on the particle surface and the structure represented by formula (1) need not be necessarily bonded directly but may be bonded through an arbitrary group.

The volume average particle diameter (when the flame-retardant particle is non-spherical, an average diameter of its circumscribed circle) of the flame-retardant particle in the third and fourth exemplary embodiments is preferably from 500 nm to 5 µm, more preferably from 600 nm to 5 µm, still more preferably from 600 nm to 1 µm. Incidentally, the volume average particle diameter is measured by a laser Doppler heterodyne particle size distribution meter (MICROTRAC-UPA150, trade name, produced by Nikkiso Co., Ltd.). If the volume average particle diameter is less than 500 nm, the flame retardance-holding capability tends to decrease when added to a resin, whereas if it exceeds 5 µm, a large amount of the flame-retardant particle needs to be added in a resin so as to obtain sufficiently high flame retardance and this tends to cause reduction in the mechanical properties of the resin formed body.

(Resin Composition)

The resin composition according to the fifth exemplary embodiment comprises a resin and the above-described flame-retardant compound and/or flame-retardant particle.

The resin used in the resin composition is not particularly limited, but examples thereof include an acrylonitrile-butadiene-styrene copolymer (ABS), methylpentene, a thermoplastic vulcanized elastomer, a thermoplastic polyurethane, a styrene-isoprene-styrene block copolymer, silicone, a styrene-ethylene-propylene-styrene block copolymer, a styrene-ethylene-butylene-styrene block copolymer, a styrene-butadiene-styrene block copolymer, a styrene-butadiene rubber, a styrene-butadiene copolymer, an acrylonitrile-styrene copolymer, polyvinylpyrrolidone, polyvinyl alcohol, polyvinyl methyl ether, polyvinyl isobutyl ether, polyvinylformal, polyvinylbutyral, polyvinyl acetate, polyvinyl alcohol, polytrimethylene terephthalate, polysulfone, polysulphone, polystyrene, polyphenylene sulfide, polyphenylene ether, polypropylene, polyphthalamide, polyoxymethylene, polymethylpentene, polymethyl methacrylate, poly-methacrylonitrile, poly-methoxyacetal, polyisobutylene, thermoplastic polyimide, polyethylene terephthalate, polyether sulfone, polyethylene naphthalate, polyether nitrile, polyether imide, polyether ether ketone, polyethylene, polycarbonate, polybutylene terephthalate, polybutadiene styrene, polyparaphenylene benzobisoxazole, poly-n-butyl methacrylate, polybenzimidazole, polybutadiene acrylonitrile, polybutene-1, polyallylsulfone, polyallylate, polyacrylonitrile, a thermoplastic polyester alkyd resin, thermoplastic polyamide-imide, polyacrylic acid, polyamide, natural rubber, nitrile rubber, a methyl methacrylate-butadiene-styrene copolymer, polyethylene, isoprene rubber, ionomer, butyl rubber, a furan resin, an ethylene-vinyl alcohol copolymer, an ethylene-vinyl acetate copolymer, an ethylene-propylene-diene ternary copolymer, cellulose propionate, hydrin rubber, carboxymethyl cellulose, a cresol resin, cellulose acetate propionate, cellulose acetate butyrate, cellulose acetate, bismaleimide triazine, cis-1•4-polybutadiene synthetic rubber, acrylonitrile-styrene-acrylate, an acrylonitrile-styrene copolymer, an acrylonitrile-ethylene-propylene-styrene copolymer, acrylic acid ester rubber, and polylactic acid. One of these resins is used alone, or two or more species thereof are used in combination.

In the resin composition according to this exemplary embodiment, the total content of the flame-retardant compound and/or flame-retardant particle is preferably from 1 to 100 parts by mass, more preferably from 5 to 50 parts by mass, per 100 parts by mass of the resin. If this content is less than 1 part by mass, insufficient flame retardance tends to result, whereas if it exceeds 100 parts by mass, the mechanical strength of the resin formed body obtained is liable to decrease.

Incidentally, the resin composition according to this exemplary embodiment may further contain a flame retarder other than the above-described flame-retardant compound and/or flame-retardant particle (hereinafter, for the sake of convenience, this flame retarder is referred to as "other flame retarders") as long as the effect of the resin composition is not impaired. Examples of other flame retarders include a phosphorus-based flame retarder, a bromine-based flame retarder, a silicone-based flame retarder, and an inorganic particle-based flame retarder. From the standpoint of satisfying both the flame retardance and the mechanical strength, the total content of other flame retarders is preferably 10 mass % or less, more preferably 5 mass % or less, based on the entire solid content of the resin composition, and it is still more preferred not to contain other flame retarders.

Also, the resin composition according to this exemplary embodiment may further contain an additive such as antioxidant, reinforcing agent, compatibilizer, weathering agent, reinforcement and hydrolysis inhibitor, a catalyst and the like, if desired. The content of each of these additives and catalyst is preferably 5 mass % or less based on the entire solid content of the resin composition.

(Resin Formed Body)

The resin formed body according to the sixth exemplary embodiment comprises a resin and the above-described flame-retardant compound and/or flame-retardant particle. Also, the rein formed body is obtained by shaping the above-described resin composition. Incidentally, the constituent components of the resin formed body according to this exemplary embodiment are the same as the constituent components of the resin composition according to the fifth exemplary embodiment, and their redundant description is omitted here.

The resin formed body according to this exemplary embodiment is obtained, for example, by shaping the above-described resin composition by a known method such as injection molding, injection compression molding, press molding, extrusion molding, blow molding, calendar molding, coating molding, cast molding or dipping molding.

The resin formed body according to this exemplary embodiment is not particularly limited in its usage, but examples of the usage include a casing or various parts of home electric appliances, office equipment or the like, a wrapping film, a housing box of CD-ROM, DVD or the like, tableware, a food tray, a beverage bottle, and a medical wrapping material.

FIG. 1 is a view showing one example of an image forming apparatus comprising a casing produced using the resin formed body according to this exemplary embodiment and office equipment parts, and this is an outer appearance perspective view when the image forming apparatus is seen from the front side. In FIG. 1, the image forming apparatus 100 comprises front covers 120a and 120b at the front of a main body apparatus 110. These front covers 120a and 120b are openable/closable so that an operator can operate the inside of the apparatus. By this construction, the operator can replenish the toner when the toner is consumed, replace the wasted process cartridge, or remove the jammed paper on occurrence of paper jamming inside of the apparatus. FIG. 1 shows the apparatus in a state of the front covers 120a and 120b being opened.

On the top of the main body apparatus 110, an operation panel 130 into which various conditions concerning the image formation, such as paper size and number of sheets, are input through the operation by an operator, and a copy glass 132 on which the original to be read is placed, are provided. The main body apparatus 110 also comprises, at the upper part thereof, an automatic original conveying device 134 capable of automatically conveying the original onto the copy glass 132. Furthermore, the main body apparatus 110 comprises an image reading device for scanning the original image disposed on the copy glass 132 and obtaining image data for reproducing the original image. The image data obtained by this image reading device are sent to an image forming unit through a control part. The image reading device and the control part are housed inside a casing 150 constituting a part of the main body apparatus 110. Also, the image forming unit is provided as a removable process cartridge 142 in the casing 150. The process cartridge 142 can be loaded or removed by turning an operation lever 144.

In the casing 150 of the main body apparatus 110, a toner housing part 146 is fixed, and a toner is replenished from a toner feed port 148. The toner housed in the toner housing part 146 is fed to a developing device.

In the lower part of the main body apparatus 110, paper housing cassettes 140a, 140b and 140c are provided. Also, in the main body apparatus 110, a plurality of conveying rollers each composed of a pair of rollers are arrayed inside of the apparatus, whereby a conveying path allowing the paper in the paper housing cassette to be conveyed to the image forming unit located above the cassette is formed. The paper in each paper housing cassette is taken out one by one by a paper take-out mechanism disposed near the end of the conveying path and delivered to the conveying path. A paper tray 136 for manual feeding is provided on the side surface of the main body apparatus 110, and the paper is fed also from this tray, if desired.

The paper on which an image is formed by the image forming unit is sequentially transferred between two fixing rolls abutting against each other and being supported by a casing 152 constituting a part of the main body apparatus 110 and then discharged outside the main body apparatus 110. In the main body apparatus 110, a plurality of discharge trays 138 are provided on the side opposite the side where the paper tray 136 is provided, and the paper after image formation is discharged to these trays.

In the image forming apparatus 100, the front covers 120a and 120b are often subject to a load such as stress and impact at the opening/closing, vibration during image formation, and heat generated inside of the image forming apparatus. Also, the process cartridge 142 is often subject to a load such as impact at the loading/removal, vibration during image formation, and heat generated inside of the image forming apparatus. Furthermore, the casing 150 and the casing 152 are often subject to a load such as vibration during image formation and heat generated inside of the image forming apparatus. Therefore, the resin formed body according to this exemplary embodiment is suitably used as the front covers 120a and 120b of the image forming apparatus 100, the exterior of the process cartridge 142, the casing 150 and the casing 152.

EXAMPLES

The exemplary embodiment of the present invention is described in greater detail below by referring to Examples and Comparative Examples, but the exemplary embodiment of the present invention is not limited to the following Examples.

Example 1

A stirrer is placed in a 1,000 ml-volume glass flask and after introducing 20 g of hydroquinone, the inside of the vessel is replaced with nitrogen. Thereto, 300 ml of dehydrated tetrahydrofuran and 70 ml of dehydrated triethylamine are added to dissolve the hydroquinone. Subsequently, while cooling the inside of the system by using an ice bath, 50 ml of phenyl chloroformate is slowly added. Thereafter, the mixture is stirred at room temperature for 6 hours, and the reaction is stopped by charging 50 ml of methanol. The objective material is precipitated by charging the reaction solution into a large amount of methanol, then recovered by filtration and further washed with methanol several times, whereby Flame-Retardant Compound A represented by the following formula (3) is obtained.

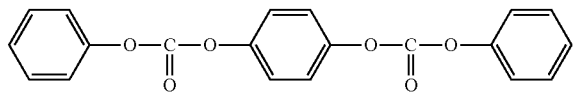

(3)

Subsequently, 50 parts by mass of the obtained Flame-Retardant Compound A is added to 100 parts by mass of ABS resin (AT-05, trade name, produced by Nippon A&L Inc.), and the blend is melt-mixed at 180° C. in a twin-screw extruder and further melt-shaped by a press at 200° C. to produce a UL-94 burning test specimen (width: 13 mm, length: 125 mm, thickness: 2.0 mm).

Example 2

A stirrer is placed in a 1,000 ml-volume glass flask and after introducing 25 g of phloroglucinol, the inside of the vessel is replaced with nitrogen. Thereto, 300 ml of dehydrated tetrahydrofuran and 120 ml of dehydrated triethylamine are added to dissolve the phloroglucinol. Subsequently, while cooling the inside of the system by using an ice bath, 100 ml of phenyl chloroformate is slowly added. Thereafter, the mixture is stirred at room temperature for 6 hours, and the reaction is stopped by charging 100 ml of methanol. The objective material is precipitated by charging the reaction solution into a large amount of methanol, then recovered by filtration and further washed with methanol several times, whereby Flame-Retardant Compound B represented by the following formula (4) is obtained.

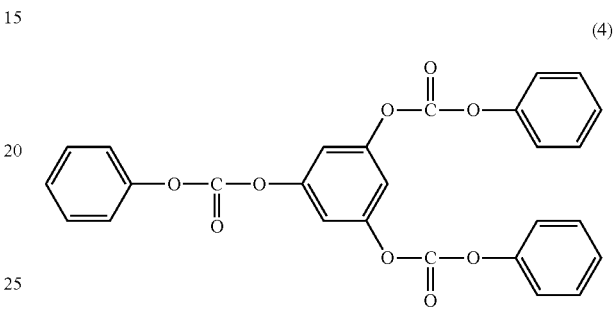

(4)

Subsequently, 50 parts by mass of the obtained Flame-Retardant Compound B is added to 100 parts by mass of ABS resin (AT-05, trade name, produced by Nippon A&L Inc.), and the blend is melt-mixed and then melt-shaped under the same conditions as in Example 1 to produce a UL-94 burning test specimen (width: 13 mm, length: 125 mm, thickness: 2.0 mm).

Example 3

A stirrer is placed in a 1,000 ml-volume glass flask and after introducing 25 g of hydroxybenzenesulfonic acid, the inside of the vessel is replaced with nitrogen. Thereto, 300 ml of dehydrated tetrahydrofuran and 120 ml of dehydrated triethylamine are added to dissolve the hydroxybenzenesulfonic acid. Subsequently, while cooling the inside of the system by using an ice bath, 40 ml of phenyl chloroformate is slowly added. Thereafter, the mixture is stirred at room temperature for 6 hours, and the reaction is stopped by charging 40 ml of methanol. The objective material is precipitated by charging the reaction solution into a large amount of methanol, then recovered by filtration and further washed with methanol several times, whereby Flame-Retardant Compound C represented by the following formula (5) is obtained.

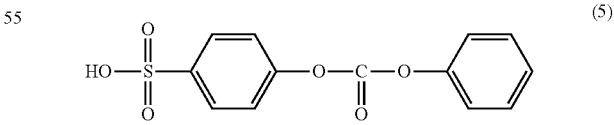

(5)

Subsequently, 50 parts by mass of the obtained Flame-Retardant Compound C is added to 100 parts by mass of ABS resin (AT-05, trade name, produced by Nippon A&L Inc.), and the blend is melt-mixed and then melt-shaped under the same conditions as in Example 1 to produce a UL-94 burning test specimen (width: 13 mm, length: 125 mm, thickness: 2.0 mm).

Example 4

A stirrer is placed in a 1,000 ml-volume glass flask and after introducing 25 g of bisphenol S, the inside of the vessel is replaced with nitrogen. Thereto, 300 ml of dehydrated tetrahydrofuran and 100 ml of dehydrated triethylamine are added to dissolve the bisphenol S. Subsequently, while cooling the inside of the system by using an ice bath, 80 ml of phenyl chloroformate is slowly added. Thereafter, the mixture is stirred at room temperature for 6 hours, and the reaction is stopped by charging 80 ml of methanol. The objective material is precipitated by charging the reaction solution into a large amount of a methanol/water mixed solution (mass ratio: 70/30), then recovered by filtration and further washed with methanol several times, whereby Flame-Retardant Compound D represented by the following formula (6) is obtained.

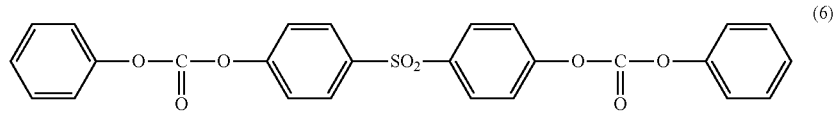

(6)

Subsequently, 50 parts by mass of the obtained Flame-Retardant Compound D is added to 100 parts by mass of ABS resin (AT-05, trade name, produced by Nippon A&L Inc.), and the blend is melt-mixed and then melt-shaped under the same conditions as in Example 1 to produce a UL-94 burning test specimen (width: 13 mm, length: 125 mm, thickness: 2.0 mm).

Example 5

Silica particle is treated with vinyltriethoxysilane to introduce a vinyl group into the particle surface. Subsequently, a paratoluenesulfonic acid catalyst is added, the temperature is elevated to 130° C., and then the vinyl group-introduced silica particle prepared above is added and reacted for 1 hour. After the completion of reaction, the reaction product is washed with methanol and then filtered to obtain a phenol-introduced silica particle.

A stirrer is placed in a 500 ml-volume glass flask and after introducing 20 g of the phenol-introduced silica particle prepared above, the inside of the vessel is replaced with nitrogen. Thereto, 300 ml of dehydrated tetrahydrofuran and 70 ml of dehydrated triethylamine are added. Subsequently, while cooling the inside of the system by using an ice bath, 50 ml of phenyl chloroformate is slowly added. Thereafter, the mixture is stirred at room temperature for 6 hours, and the reaction is stopped by charging 50 ml of methanol. The reaction solution is charged into a large amount of methanol, and the objective material is recovered by filtration and further washed with methanol several times, whereby Flame-Retardant Particle E in which a structure represented by the following formula (7) is introduced into the silica particle surface is obtained.

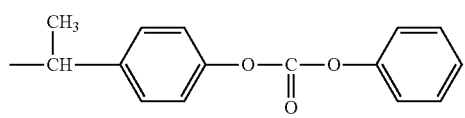

(7)

Subsequently, 50 parts by mass of the obtained Flame-Retardant Particle E is added to 100 parts by mass of ABS resin (AT-05, trade name, produced by Nippon A&L Inc.), and the blend is melt-mixed and then melt-shaped under the same conditions as in Example 1 to produce a UL-94 burning test specimen (width: 13 mm, length: 125 mm, thickness: 2.0 mm).

Example 6

Silica particle is treated with 3-glycidoxypropyltrimethoxysilane to introduce an epoxy group into the particle surface. A stirrer is placed in a 500 ml-volume glass flask and after introducing 20 g of 4-aminophenol, the inside of the vessel is replaced with nitrogen. Thereto, 300 ml of dehydrated tetrahydrofuran and 70 ml of dehydrated triethylamine are added to dissolve the 4-aminophenol. Subsequently, while cooling the inside of the system by using an ice bath, 50 ml of phenyl chloroformate is slowly added. Thereafter, the mixture is stirred at room temperature for 6 hours, and the reaction is stopped by charging 50 ml of methanol. The reaction solution is charged into a large amount of methanol to obtain a compound represented by the following formula (8).

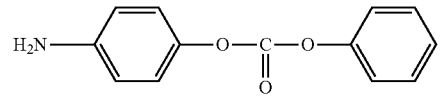

(8)

Furthermore, 15 g of this compound is dissolved in 100 ml of tetrahydrofuran, and 10 g of the epoxy group-introduced silica particle prepared above is added and reacted at 50° C. for 10 hours, whereby Flame-Retardant Particle F in which a structure represented by the following formula (9) is introduced into the silica particle surface is obtained.

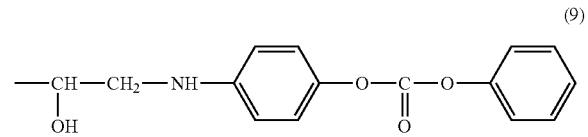

(9)

Subsequently, 50 parts by mass of the obtained Flame-Retardant Particle F is added to 100 parts by mass of ABS resin (AT-05, trade name, produced by Nippon A&L Inc.), and the blend is melt-mixed and then melt-shaped under the same conditions as in Example 1 to produce a UL-94 burning test specimen (width: 13 mm, length: 125 mm, thickness: 2.0 mm).

Example 7

Hydroquinone (35 g) and 0.35 g of a paratoluenesulfonic acid catalyst are added to 150 ml of methyl ethyl ketone and after elevating the temperature to 130° C., 41 g of divinylbenzene is added dropwise and reacted for 6 hours. After the completion of reaction, the reaction product is washed with methanol and filtered to obtain a compound having a repeating unit represented by the following formula (10).

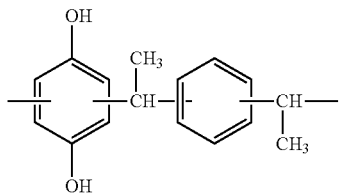

(10)

A stirrer is placed in a 1,000 ml-volume glass flask and after introducing 35 g of the compound having a repeating unit represented by formula (10), the inside of the vessel is replaced with nitrogen. Thereto, 300 ml of dehydrated tetrahydrofuran and 70 ml of dehydrated triethylamine are added. Subsequently, while cooling the inside of the system by using an ice bath, 60 ml of phenyl chloroformate is slowly added. Thereafter, the mixture is stirred at room temperature for 6 hours, and the reaction is stopped by charging 50 ml of methanol. The reaction solution is charged into a large amount of methanol, and the objective material is recovered by filtration and further washed with methanol several times, whereby Flame-Retardant Compound H represented by the following formula (11) is obtained.

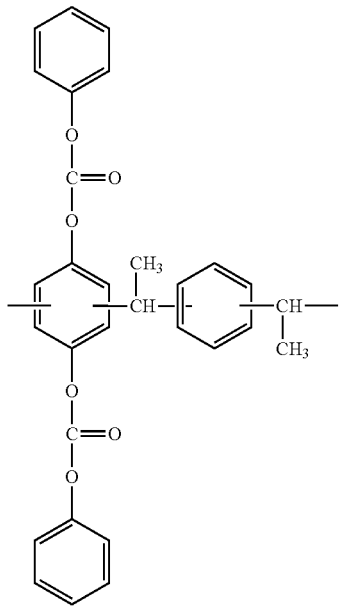

(11)

Subsequently, 50 parts by mass of the obtained Flame-Retardant Compound H is added to 100 parts by mass of ABS resin (AT-05, trade name, produced by Nippon A&L Inc.), and the blend is melt-mixed and then melt-shaped under the same conditions as in Example 1 to produce a UL-94 burning test specimen (width: 13 mm, length: 125 mm, thickness: 2.0 mm).

Comparative Example 1

Flame-Retardant Particle G (weight average molecular weight: 10,000) having a repeating unit represented by the following formula (12) is obtained in the same manner as in Example 3 except for using 25 g of poly(4-vinylphenol (produced by Maruzen Kagaku, weight average molecular weight: about 5,000) in place of 25 g of hydroxybenzenesulfonic acid.

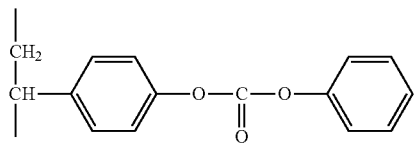

(12)

Subsequently, 50 parts by mass of the obtained Flame-Retardant Particle G is added to 100 parts by mass of ABS resin (AT-05, trade name, produced by Nippon A&L Inc.), and the blend is melt-mixed and then melt-shaped under the same conditions as in Example 1 to produce a UL-94 burning test specimen (width: 13 mm, length: 125 mm, thickness: 2.0 mm).

Comparative Example 2

50 Parts by mass of hydroquinone is added to 100 parts by mass of ABS resin (AT-05, trade name, produced by Nippon A&L Inc.), and the blend is melt-mixed and then melt-shaped under the same conditions as in Example 1 to produce a UL-94 burning test specimen (width: 13 mm, length: 125 mm, thickness: 2.0 mm).

Comparative Example 3

50 Parts by mass of phloroglucinol is added to 100 parts by mass of ABS resin (AT-05, trade name, produced by Nippon A&L Inc.), and the blend is melt-mixed and then melt-shaped under the same conditions as in Example 1 to produce a UL-94 burning test specimen (width: 13 mm, length: 125 mm, thickness: 2.0 mm).

Comparative Example 4

50 Parts by mass of bisphenol S is added to 100 parts by mass of ABS resin (AT-05, trade name, produced by Nippon A&L Inc.), and the blend is melt-mixed and then melt-shaped under the same conditions as in Example 1 to produce a UL-burning test specimen (width: 13 mm, length: 125 mm, thickness: 2.0 mm).

<Measurement of Residual Ratio>

Flame-Retardant Compounds A to D and G, Flame-Retardant Particles E and F, hydroquinone, phloroglucinol and bisphenol S are subjected to a thermogravimetric analysis (TGA) as follows. That is, by using TGA-DTA2000S (trade name) manufactured by Seiko, the temperature is elevated from room temperature to 600° C. at a temperature rise rate of 20° C./min in a nitrogen stream and the residual ratio at 600° C. is measured. The results obtained are shown in Table 1.

TABLE 1

| | Residual Ratio at 600° C. (mass %) |
|---|---|
| Flame-Retardant Compound A | 7.6 |
| Flame-Retardant Compound B | 13.2 |
| Flame-Retardant Compound C | 6.2 |
| Flame-Retardant Compound D | 22.5 |

TABLE 1-continued

| | Residual Ratio at 600° C. (mass %) |
|---|---|
| Flame-Retardant Particle E | 75.3 |
| Flame-Retardant Particle F | 76.2 |
| Flame-Retardant Compound G | 12.8 |
| Flame-Retardant Compound H | 13.4 |
| Hydroquinone | 0 |
| Phloroglucinol | 0 |
| Bisphenol S | 13.5 |

<Evaluation of Flame Retardance>

UL-94 Burning test specimens produced above are tested by a UL-94 vertical burning test and rated by four ranks of V-0, V-1, V-2 and burned according to the criteria of UL-94 Standards. The results obtained are shown in Table 2.

<Evaluation of Mechanical Strength (Charpy Impact Strength>

UL-94 Burning test specimens produced above are measured for the Charpy impact strength according to JIS K7111. The results obtained are shown in Table 2.

TABLE 2

| | Flame Retardance | Charpy Impact Strength (KJ/m$^2$) |
|---|---|---|
| Example 1 | V-2 | 7 |
| Example 2 | V-2 | 8 |
| Example 3 | V-2 | 7 |
| Example 4 | V-2 | 7 |
| Example 5 | V-2 | 6 |
| Example 6 | V-2 | 6 |
| Example 7 | V-2 | 8 |
| Comparative Example 1 | burned | 4 |
| Comparative Example 2 | burned | 3 |
| Comparative Example 3 | burned | 3 |
| Comparative Example 4 | burned | 4 |

The foregoing description of the exemplary embodiments of the present invention has been provided for the purpose of illustration and description. It is not intended to be exhaustive or to limit the invention to the precise forms disclosed. Obviously, many modifications and variations will be apparent to practitioners skilled in the art. The exemplary embodiments are chosen and described in order to best explain the principles of the invention and its practical applications, thereby enabling others skilled in the art to understand the invention for various exemplary embodiments and with the various modifications as are suited to the particular use contemplated. It is intended that the scope of the invention be defined by the following claims and their equivalents.

What is claimed is:

1. The flame-retardant compound that has a structure represented by formula (2):

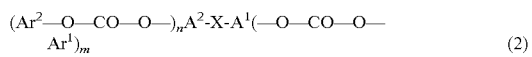

(2)

wherein $A^1$ and $A^2$ each independently represents a substituted or unsubstituted aromatic group;

X represents a divalent group represented by —S—, —O—, —CO—, —CN—, —CH$_2$—, —C(CH$_3$)$_2$—, —CH(CH$_3$)—, —NH—, —SO— or —SO$_2$—;

$Ar^1$ and $Ar^2$ each independently represents a substituted or unsubstituted phenyl group; and m represents an integer of 2 to 3, and n represents an integer of 1 to 3.

2. The flame-retardant compound according to claim 1, wherein $A^1$ and $A^2$ each independently represents an aromatic group having at least one substituent selected from the group consisting of an alkyl group having a carbon number of 1 to 10, a phenyl group, an alkoxyl group, an amino group, an amido group, an aryl group, an acyl group, a vinyl group, an allyl group, a hydroxy group, an ester group and a carboxyl group.

3. The flame-retardant compound according to claim 1, wherein $Ar^1$ and $Ar^2$ each independently represents a phenyl group having at least one substituent selected from the group consisting of an alkyl group having a carbon number of 1 to 10, a phenyl group, an alkoxyl group, an amino group, an amido group, an aryl group, an acyl group, a vinyl group, an allyl group, a hydroxy group, an ester group and a carboxyl group.

4. The flame-retardant compound according to claim 1, wherein n represents an integer of 2 to 3.

5. The flame-retardant particle that has a structure represented by formula (2) introduced into a surface thereof:

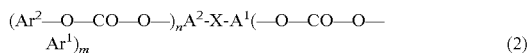

(2)

wherein $A^1$ and $A^2$ each independently represents a substituted or unsubstituted aromatic group;

X represents a divalent group represented by —S—, —O—, —CO—, —CN—, —CH$_2$—, —C(CH$_3$)$_2$—, —CH(CH$_3$)—, —NH—, —SO— or —SO$_2$—;

$Ar^1$ and $Ar^2$ each independently represents a substituted or unsubstituted phenyl group; and m represents an integer of 2 to 3, and n represents an integer of 1 to 3.

6. The flame-retardant particle according to claim 5, comprising:

a core particle containing at least one selected from the group consisting of an inorganic material, an inorganic material complex, an organic polymer, a dendrimer, clay, fullerene or carbon nanotube.

7. The flame-retardant particle according to claim 6, wherein the core particle has at least one functional group selected from the group consisting of a hydroxyl group, a carboxyl group, an amino group, an aldehyde group, a vinyl group, a carbonyl group, a nitro group, a sulfo group, an ether group, an ester group, an amide group, an isocyanate group, a halogen group, an alkyl group and a cyano group on a surface thereof.

8. The flame-retardant particle according to claim 5, which has a volume average particle diameter of from 500 nm to 5 µm.

9. The flame-retardant particle according to claim 5, comprising:

a surface coat layer on the core particle, the surface coat layer containing the structure represented by formula (2).

10. The flame-retardant particle according to claim 9, wherein a coverage of the surface coat layer is 5 mass % or more of the entire flame-retardant particle.

11. The flame-retardant particle according to claim 9, wherein the core particle is a porous particle, and pores of the porous particle are filled with a constituent material of the surface coat layer.

12. The flame-retardant particle according to claim 9, further comprising:

a layer other than the surface coat layer on the core particle.

13. A resin composition, comprising:
a resin; and
at least one of:
a flame-retardant compound that has a structure represented by formula (2):

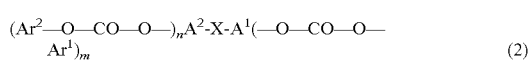

wherein $A^1$ and $A^2$ each independently represents a substituted or unsubstituted aromatic group;
X represents a divalent group represented by —S—, —O—, —CO—, —CN—, —CH$_2$—, —C(CH$_3$)$_2$—, —CH(CH$_3$)—, —NH—, —SO— or —SO$_2$—;
$Ar^1$ and $Ar^2$ each independently represents a substituted or unsubstituted phenyl group; and
m represents an integer of 2 to 3, and n represents an integer of 1 to 3, and
a flame-retardant particle that has a structure represented by formula (2) introduced into a surface thereof:

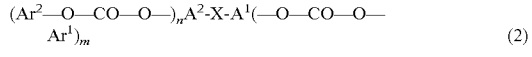

wherein $A^1$ and $A^2$ each independently represents a substituted or unsubstituted aromatic group;
X represents a divalent group represented by —S—, —O—, —CO—, —CN—, —CH$_2$—, —C(CH$_3$)$_2$—, —CH(CH$_3$)—, —NH—, —SO— or —SO$_2$—;
$Ar^1$ and $Ar^2$ each independently represents a substituted or unsubstituted phenyl group; and
m represents an integer of 2 to 3, and n represents an integer of 1 to 3.

14. The resin composition according to claim 13,
wherein a total content of the at least one of the flame-retardant compound and the flame-retardant particle is from 1 to 100 parts by mass, per 100 parts by mass of the resin.

15. The resin composition according to claim 13, further comprising:
a flame retarder other than the at least one of the flame-retardant compound and the flame-retardant particle.

16. The resin composition according to claim 15,
wherein the flame retarder is at least one selected from the group consisting of a phosphorus-based flame retarder, a bromine-based flame retarder, a silicone-based flame retarder and an inorganic particle-based flame retarder.

17. The resin composition according to claim 15,
wherein a total content of the flame retarder is 10 mass % or less based on an entire solid content of the resin composition.

18. A resin formed body, comprising:
a resin; and
at least one of:
a flame-retardant compound that has a structure represented by formula (2):

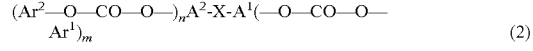

wherein $A^1$ and $A^2$ each independently represents a substituted or unsubstituted aromatic group;
X represents a divalent group represented by —S—, —O—, —CO—, —CN—, —CH$_2$—, —C(CH$_3$)$_2$—, —CH(CH$_3$)—, —NH—, —SO— or —SO$_2$—;
$Ar^1$ and $Ar^2$ each independently represents a substituted or unsubstituted phenyl group; and
m and n each independently represents an integer of 1 to 3, and
a flame-retardant particle that has a structure represented by formula (2) introduced into a surface thereof:

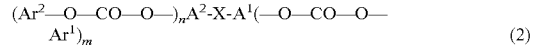

wherein $A^1$ and $A^2$ each independently represents a substituted or unsubstituted aromatic group;
X represents a divalent group represented by —S—, —O—, —CO—, —CN—, —CH$_2$—, —C(CH$_3$)$_2$—, —CH(CH$_3$)—, —NH—, —SO— or —SO$_2$—;
$Ar^1$ and $Ar^2$ each independently represents a substituted or unsubstituted phenyl group; and
m represents an integer of 2 to 3, and n represents an integer of 1 to 3.

19. The resin formed body according to claim 18,
wherein a total content of the at least one of the flame-retardant compound and the flame-retardant particle is from 1 to 100 parts by mass, per 100 parts by mass of the resin.

20. The resin formed body according to claim 18, further comprising:
a flame retarder other than the at least one of the flame-retardant compound and the flame-retardant particle.

21. The resin formed body according to claim 20,
wherein the flame retarder is at least one selected from the group consisting of a phosphorus-based flame retarder, a bromine-based flame retarder, a silicone-based flame retarder and an inorganic particle-based flame retarder.

22. The resin formed body according to claim 20,
wherein a total content of the flame retarder is 10 mass % or less based on an entire solid content of the resin formed body.

* * * * *